US012668579B2

(12) United States Patent
March et al.

(10) Patent No.: US 12,668,579 B2
(45) Date of Patent: Jun. 30, 2026

(54) (3aS,4aR,5S,7aS,9R,9aR)-2,2,5,8,8,9a-HEXAMETHYLOCTAHYDRO-4H-4a,9-METHANOAZULENO[5,6-d][1,3]DIOXOLE

(71) Applicant: Givaudan SA, Vernier (CH)

(72) Inventors: Sébastien March, Carouge (CH); Gerhard Brunner, Opfikon (CH); Julie Charpentier, Zurich (CH); Heinz Koch, Baeretswil (CH); Veronika Zelenay, Kemptthal (CH)

(73) Assignee: GIVAUDAN SA, Vernier (CH)

( * ) Notice: Subject to any disclaimer, the term of this patent is extended or adjusted under 35 U.S.C. 154(b) by 660 days.

(21) Appl. No.: 18/124,762

(22) Filed: Mar. 22, 2023

(65) Prior Publication Data

US 2023/0219918 A1 Jul. 13, 2023

Related U.S. Application Data

(63) Continuation of application No. 17/434,147, filed as application No. PCT/EP2019/056332 on Mar. 13, 2019, now Pat. No. 11,634,402.

(51) Int. Cl.

| | |
|---|---|
| ***C07D 317/70*** | (2006.01) |
| ***A61K 8/49*** | (2006.01) |
| ***C11B 9/00*** | (2006.01) |

(52) U.S. Cl.

CPC .......... *C07D 317/70* (2013.01); *C11B 9/0042* (2013.01); *C11B 9/0076* (2013.01); *C07B 2200/09* (2013.01); *C07B 2200/13* (2013.01)

(58) Field of Classification Search

CPC ..... A61Q 19/10; C11B 9/0076; C11B 9/0042; C07B 2200/09; C07B 2200/13; C07D 317/70; A61K 8/498

USPC .......................................................... 512/12

See application file for complete search history.

(56) References Cited

U.S. PATENT DOCUMENTS

| | | | | |
|---|---|---|---|---|
| 11,066,625 | B2 * | 7/2021 | Eh | A61K 8/37 |
| 2008/0161224 | A1 * | 7/2008 | Naraschkewitz | C11B 9/0034 512/12 |
| 2012/0077722 | A1 | 3/2012 | Dilk et al. | |
| 2017/0114299 | A1 * | 4/2017 | Schatkowski | C07D 317/70 |
| 2020/0172830 | A1 | 6/2020 | Eh et al. | |
| 2020/0239810 | A1 | 7/2020 | Betzer et al. | |

FOREIGN PATENT DOCUMENTS

| | | | |
|---|---|---|---|
| WO | 2006058450 | A2 | 6/2006 |
| WO | 2010000083 | A1 | 1/2010 |
| WO | 2017186973 | A2 | 11/2017 |

OTHER PUBLICATIONS

Triller et al., Odorant-receptor interactions and odor percept: a chemical perspective, 2008, Chemistry and Biochemistry, vol. 5, 862-886 (Year: 2008).*

Roucel et al., The importance of New Molecules in Selective Perfumery, 2014, Chemistry and Biodiversity, vol. 11, 1462-1469 (Year: 2014).*

Chapter 10: Everyday chemical essences, Part 1: Flavour type characteristics and reference usage amounts of everyday chemical essences with different uses, Practical Handbook of Cosmetic Ingredient Specifications, edited by Dianyi Zhang, published in 2002.

"Physical and Chemical Biosensors", p. 431, edited by Xinbao Ning and Depei Huang, published in 1991.

International Search Report for Application No. PCT/EP2019/056332 dated May 31, 2019.

Written Opinion for Application No. PCT/EP2019/056332 dated May 31, 2019.

Andersen, et al., "The Absolute Stereochemistry of the Alaskenes and Acorone-Related Sesquiterpenes", Tetrahedron Letters No. 10, pp. 899-902, 1972. Pergamon Press, Great Britain.

Anubhav P. S. Narula, "The Search for New Amber Ingredients", Chemistry & Biodiversity, vol. 11, 2014, pp. 1629-1638.

Roucel, et al., "The Importance of New Molecules in Selective Perfumery", Chemistry & Biodiversity, vol. 11, 2014, pp. 1462-1469.

* cited by examiner

*Primary Examiner* — Jessica Whiteley

(74) *Attorney, Agent, or Firm* — Curatolo Sidoti & Trillis Co., L.P.A.; Floyd Trillis, III; Salvatore A. Sidoti

(57) ABSTRACT

The compound (3aS,4aR,5S,7aS,9R,9aR)-2,2,5,8,8,9a-hexamethyloctahydro-4H-4a,9-methanoazuleno[5,6-d][1,3]dioxole, compositions and consumer products comprising the compound, methods of making the compound, and the various uses of the compound.

7 Claims, 1 Drawing Sheet

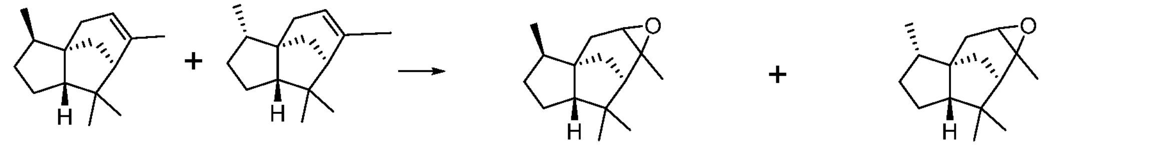

(-)-alpha-cedrene + epi-(-)-alpha-cedrene (VIII) → (-)-alpha-Cedrene epoxide + epi-(-)-alpha-Cedrene epoxide (IX)

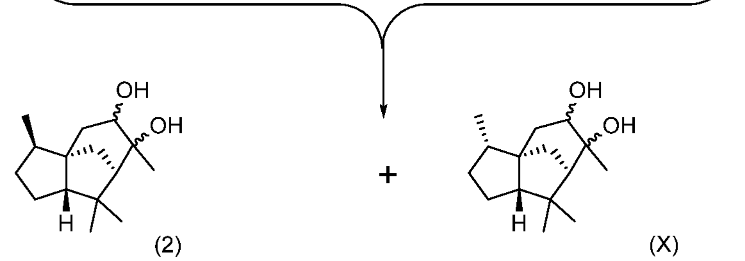

(2) + (X)

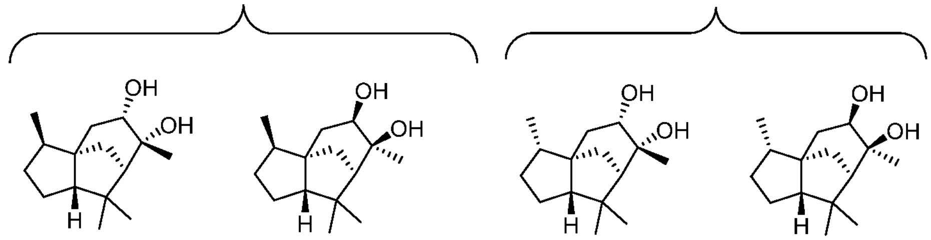

syn-diol (2a) + syn-diol (2b) syn-epi-diol (Xa) + syn-epi-diol (Xb)

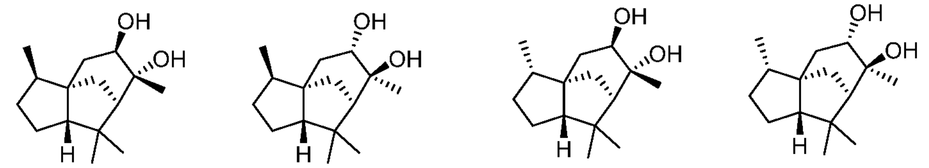

anti-diol (2c) anti-diol (2d) anti-epi-diol (Xc) anti-epi-diol (Xd)

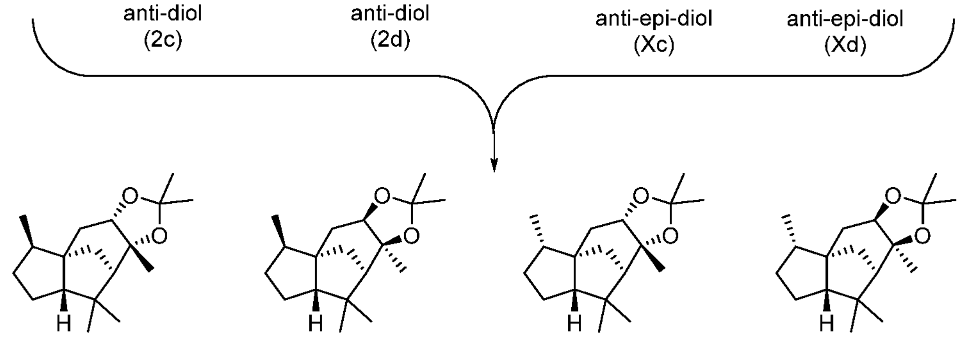

syn-Ambrocenide® (II) + syn-Ambrocenide® (III) syn-epi-Ambrocenide® (I) + syn-epi-Ambrocenide® (XI)

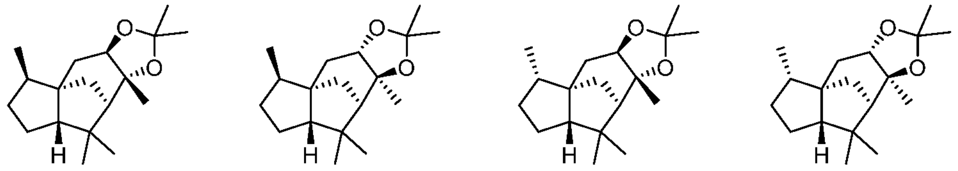

anti-Ambrocenide® (IV) anti-Ambrocenide® (V) anti-epi-Ambrocenide® (XII) anti-epi-Ambrocenide® (XIII)

(3aS,4aR,5S,7aS,9R,9aR)-2,2,5,8,8,9a-HEXAMETHYLOCTAHYDRO-4H-4a,9-METHANOAZULENO[5,6-d][1,3]DIOXOLE

This is a continuation application of U.S. Ser. No. 17/434,147 filed on Aug. 26, 2021, which is a national stage application of International Application No. PCT/EP2019/056332, filed Mar. 13, 2019, which applications are incorporated herein by reference.

TECHNICAL FIELD

The present invention relates generally to the compound (3aS,4aR,5S,7aS,9R,9aR)-2,2,5,8,8,9a-hexamethyloctahydro-4H-4a,9-methanoazuleno[5,6-d][1,3]dioxole of formula (I). The present invention further relates to compositions and consumer products comprising the compound of formula (I), methods of making the compound of formula (I), and the various uses of the compound of formula (I).

BACKGROUND (4aR,5R,7aS,9R)-2,2,5,8,8,9a-hexamethyloctahydro-4H-4a,9-methanoazuleno[5,6-d][1,3]dioxole, also known as Ambrocenide®, is used as a fragrance ingredient to provide a woody and ambery odour. Ambrocenide® has been described as comprising one or more of the four diastereomers of formulas (II), (III), (IV), and (V) (see US 2017/0114299 A1 and WO 2017/186973, the contents of which are incorporated herein by reference), (II)

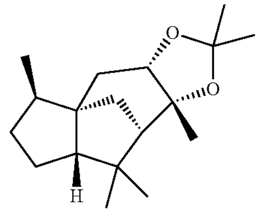

(III)

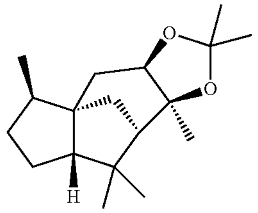

(IV)

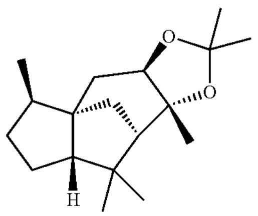

(V)

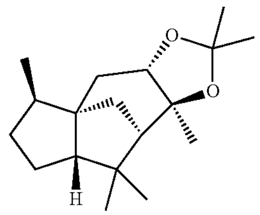

However, Ambrocenide® possesses a sharp green ambery olfactory facet which can be polarizing and limit the acceptable amount that can be used in fragrance compositions. It is therefore desirable to provide alternative or improved compounds and compositions to provide a clean woody and ambery odour profile.

SUMMARY OF THE INVENTION

In accordance with a first aspect of the present invention there is provided the compound (3aS,4aR,5S,7aS,9R,9aR)-2,2,5,8,8,9a-hexamethyloctahydro-4H-4a,9-methanoazuleno[5,6-d][1,3]dioxole of formula (I), (I)

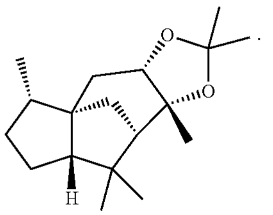

In accordance with a second aspect of the present invention there is provided a an isomeric mixture comprising the compound of formula (I) and at least one (one, two three or four) compound selected from the compounds of the formula (II), (III), (IV), and (V), (I)

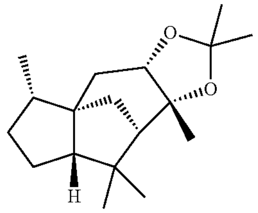

(II)

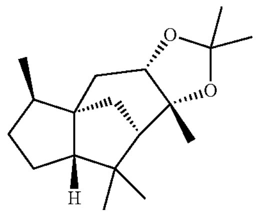

(III)

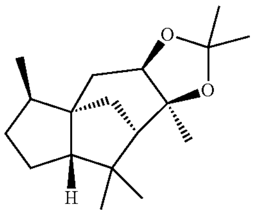

(IV)

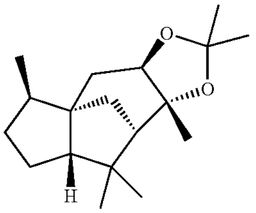

-continued (V)

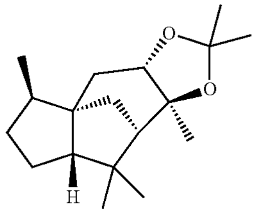

In certain embodiments, the isomeric mixture comprises a compound of formula (II). The weight ratio of the compound of formula (I) to the compound of formula (II) in the composition may range from about 0.01:99.99 to about 5:95, for example from about 0.1:99.9. to about 1:99.

In certain embodiments, the mixture does not comprise one or more of a compound of formula (III), a compound of formula (IV), and a compound of formula (V). In certain embodiments, the mixture does not comprise a compound of formula (III).

In certain embodiments, the isomeric mixture further comprises one or more of a compound selected from compound of formula (XI), (XII), and (XIII), (XI)

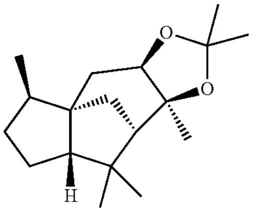

(XII)

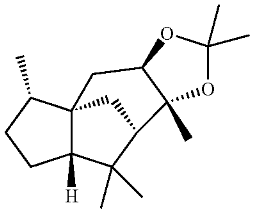

(XIII)

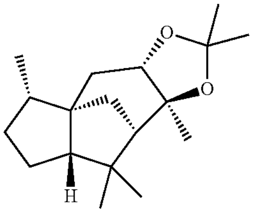

.

In accordance with a third aspect of the present invention there is provided a fragrance composition comprising the compound of the first aspect of the present invention or the isomeric mixture of the second aspect of the present invention.

In certain embodiments, the composition further comprises one or more additional known fragrance ingredients.

In certain embodiments, the composition comprises cedralone of formula (VI), for example the cedralone of formula (VIa) and/or formula (VIb), (VI)

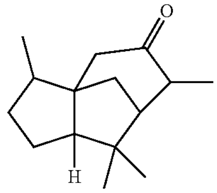

(VIa)

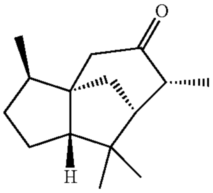

(VIb)

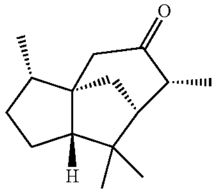

.

In accordance with a fourth aspect of the present invention there is provided a consumer product comprising the compound of the first aspect of the present invention, the isomeric mixture of the second aspect of the present invention, or the composition of the third aspect of the present invention.

In certain embodiments, the consumer product is a personal care composition. In certain embodiments, the consumer product is a cleaning product. In certain embodiments, the consumer product is a homeware composition.

In accordance with a fifth aspect of the present invention there is provided a use of the compound of the first aspect of the present invention or the mixture of the second aspect of the present invention as fragrance.

In accordance with a sixth aspect of the present invention there is provided a use of the compound of formula (I), (I)

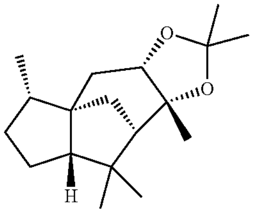

to mask or diminish one or more unpleasant olfactory impressions and/or to enhance the intensity of one or more pleasant olfactory impressions.

The one or more unpleasant olfactory impressions may, for example, be a sharp green ambery olfactory facet. The one or more pleasant olfactory impressions may, for example, be a woody and/or ambery odour.

The one or more unpleasant and/or the one or more pleasant olfactory impressions may, for example, be provided by the compound of formula (II), the compound of formula (III), the compound of formula (IV) and/or the compound of formula (V), (II)

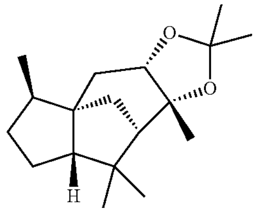

(III)

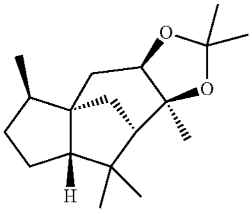

(IV)

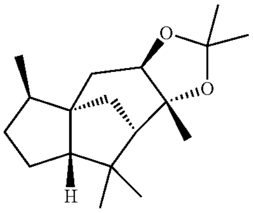

(V)

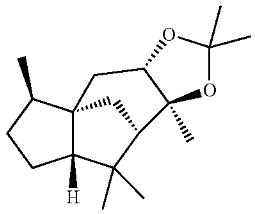

In accordance with a seventh aspect of the present invention there is provided a method of making the compound of formula (I), wherein the method comprises reacting the cedranediol of formula (Xa), or an isomeric mixture thereof (i.e. cedranediol of formula (X)), (Xa)

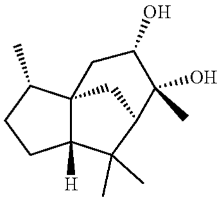

(X)

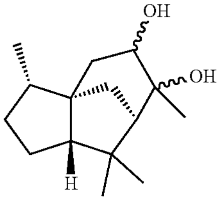

with a reactive propane derivative under suitable conditions to form the compound of formula (I), (I)

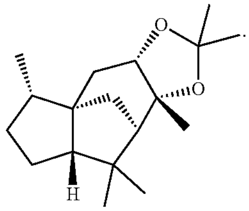

In certain embodiments, the method comprises reacting the cedranediol of formula (Xa), or an isomeric mixture thereof (i.e. cedranediol of formula (X)) with dimethoxypropane to form the compound of formula (I). This may, for example, occur under acid catalysis conditions.

In certain embodiments, the method comprises reacting the cedrene epoxide of formula (IX)

(IX)

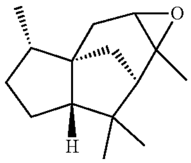

with an epoxide ring-opening agent to form the compound of formula (X).

In certain embodiments, the method comprises reacting the epi-(−) alpha-cedrene of formula (VIII), (VIII)

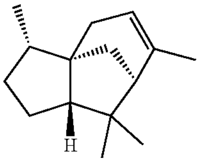

with an epoxidating agent to form the cedrene epoxide of formula (IX).

Certain embodiments of any aspect of the present invention may provide one or more of the following advantages:

- woody and/or ambery odour;
- reduced sharp green ambery olfactory facet;
- enables increased dosing of Ambrocenide® in consumer products.

The details, examples and preferences provided in relation to any particular one or more of the stated aspects of the present invention will be further described herein and apply equally to all aspects of the present invention. Any combination of the embodiments, examples and preferences described herein in all possible variations thereof is encompassed by the present invention unless otherwise indicated herein, or otherwise clearly contradicted by context.

BRIEF DESCRIPTION OF THE FIGURES

The present invention may be described with reference to the following non-limiting FIGURES in which:

FIG. 1 is a reaction scheme of the process described in Example 1 to make the compound of formula (I).

DETAILED DESCRIPTION

The present invention is based on the surprising finding that the compound (3aS,4aR,5S,7aS,9R,9aR)-2,2,5,8,8,9a-hexamethyloctahydro-4H-4a,9-methanoazuleno[5,6-d][1,3]dioxole of formula (I) reinforces the woody and ambery odour of Ambrocenide® but reduces its sharp green ambery olfactory facet.

There is therefore provided herein the compound (3aS,4aR,5S,7aS,9R,9aR)-2,2,5,8,8,9a-hexamethyloctahydro-4H-4a,9-methanoazuleno[5,6-d][1,3]dioxole of formula (I), (I)

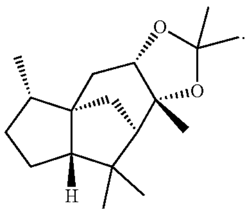

There is also provided herein a isomeric mixture comprising (3aS,4aR,5S,7aS,9R,9aR)-2,2,5,8,8,9a-hexamethyloctahydro-4H-4a,9-methanoazuleno[5,6-d][1,3]dioxole of formula (I) and at least one (one, two three or four) compound selected from the compounds of the formula (II), (III), (IV), and (V), (I)

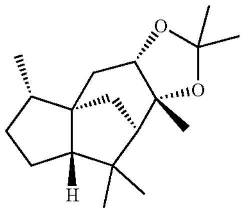

(II)

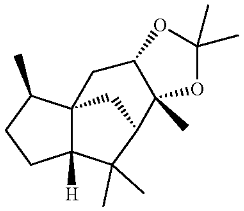

(III)

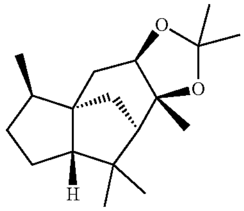

(IV)

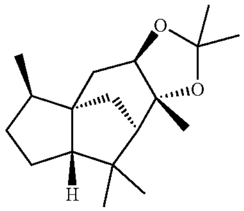

-continued (V)

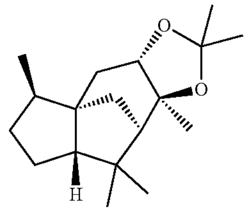

The mixture may, for example, comprise two, three, or four of the compounds selected from the compounds of formula (II), (III), (IV), and (V).

The mixture may, for example, comprise, consist essentially of, or consist of the compound of formula (I) and the compound of formula (II).

Alternatively, the mixture may, for example, comprise, consist essentially of, or consist of the compound of formula (I), the compound of formula (II), and the compound of formula (IV). The mixture may, for example, comprise, consist essentially of, or consist of the compound of formula (I), the compound of formula (II), and the compound of formula (V).

Alternatively, the mixture may, for example, comprise, consist essentially of, or consist of the compound of formula (I), the compound of formula (II), the compound of formula (IV), and the compound of formula (V). The mixture may, for example, not comprise the compound of formula (III).

The weight ratio of the compound of formula (I) to the compound of formula (II) (when present) may, for example, range from about 0.01:99.99 to about 5:95. For example, the weight ratio of the compound of formula (I) to the compound of formula (II) (when present) may range from about 0.01:99.99 to about 4:96 or from about 0.01:99.99 to about 3:97 or from about 0.01:99.99 to about 2:98 or from about 0.01:99.99 to about 1:99 or from about 0.01:99.99 to about 0.5:99.95 (e.g. about 0.2:99.8). For example, the weight ratio of the compound of formula (I) to the compound of formula (II) (when present) may range from about 0.05:99.95 to about 5:95 or from about 0.1:99.9 to about 2:98 or from about 0.5:99.5 to about 1:99.

The compound of formula (I) may be present in the mixture in an amount equal to or greater than about 0.01 wt % based on the total weight of the compounds of formulas (I), (II), (III), (IV), and (V) in the mixture. For example, the compound of formula (I) may be present in an amount equal to or greater than about 0.05 wt % or equal to or greater than about 0.1 wt % or equal to or greater than about 0.5 wt % based on the total weight of the compounds of formulas (I), (II), (III), (IV), and (V) in the mixture. The compound of formula (I) may be present in an amount equal to or less than about 5 wt % based on the total weight of the compounds of formulas (I), (II), (III), (IV), and (V) in the mixture. For example, the compound of formula (I) may be present in an amount equal to or less than about 4 wt % or equal to or less than about 3 wt % or equal to or less than about 2 wt % or equal to or less than about 1 wt % based on the total weight of the compounds of formulas (I), (II), (III), (IV), and (V) in the mixture. For example, the compound of formula (I) may be present in the mixture in an amount ranging from about 0.01 wt % to about 5 wt % or from about 0.05 wt % to about 4 wt % or from about 0.1 wt % to about 3 wt % or from about 0.2 wt % to about 2 wt % or from about 0.3 wt % to about 1 wt %.

The mixture may, for example, consist essentially of or consist of the compound of formula (I) and at least one (one, two three or four) compound selected from the compounds of the formula (II), (III), (IV), and (V). The mixture may, for example, consist essentially of or consist of the compound of formula (I) and the compound of formula (II).

The mixture may, for example, further comprise one or more of a compound of formula (XI), a compound of formula (XII), and a compound of formula (XIII), (XI)

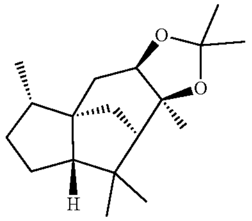

(XII)

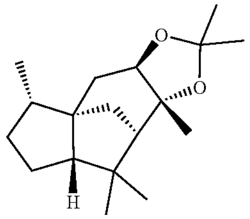

(XIII)

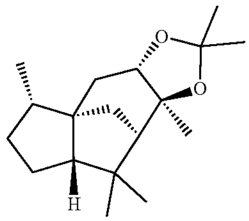

The mixture may, for example, comprise at least two compounds selected from compound of formula (XI), (XII), and (XIII).

The mixture may, for example, further comprise a compound of formula (XI) and a compound of formula (XII). The mixture may, for example, further comprise a compound of formula (XI) and a compound of formula (XIII). The mixture may, for example, further comprise a compound of formula (XII) and a compound of formula (XIII).

The term "consist essentially of" used herein means that the mixture includes at least about 90 wt % or at least about 95 wt % or at least about 98 wt % or at least about 99 wt % of the stated components. The term "consist of" used herein means that the mixture includes 100 wt % of the stated components.

There is further provided herein a composition comprising an isomeric mixture of a compound of formula (I) and at least one (one, two, three or four) compound selected from the formula (II), (III), (IV) and (V), further comprising cedralone of formula (VI), for example the cedralone of formula (VIa).

(VI)

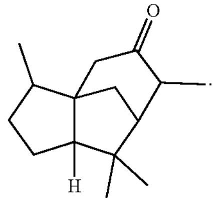

When present, the cedralone may be present in the composition in an amount ranging from about 0.01 wt % to about 1 wt % based on the total weight of the composition.

The cedralone may, for example, be a by-product of the process used for making the compound of formula (I) and/or the compound of formula (II).

The composition may further comprise additional fragrance ingredients. The following list comprises examples of known fragrance ingredients, which may be combined with the compound of formula (I):

- essential oils and extracts, e.g. castoreum, costus root oil, oak moss absolute, geranium oil, tree moss absolute, basil oil, fruit oils, such as bergamot oil and mandarine oil, myrtle oil, palmarose oil, patchouli oil, petitgrain oil, jasmine oil, rose oil, sandalwood oil, wormwood oil, lavender oil and/or ylang-ylang oil;
- alcohols, e.g. cinnamic alcohol ((E)-3-phenylprop-2-en-1-ol); cis-3-hexenol ((Z)-hex-3-en-1-ol); citronellol (3,7-dimethyloct-6-en-1-ol); dihydro myrcenol (2,6-dimethyloct-7-en-2-ol); Ebanol™ ((E)-3-methyl-5-(2,2,3-trimethylcyclopent-3-en-1-yl)pent-4-en-2-ol); eugenol (4-allyl-2-methoxyphenol); ethyl linalool ((E)-3,7-dimethylnona-1,6-dien-3-ol); farnesol ((2E,6Z)-3,7,11-trimethyldodeca-2,6,10-trien-1-ol); geraniol ((E)-3,7-dimethylocta-2,6-dien-1-ol); Super Muguet™ ((E)-6-ethyl-3-methyloct-6-en-1-ol); linalool (3,7-dimethylocta-1,6-dien-3-ol); menthol (2-isopropyl-5-methylcyclohexanol); Nerol (3,7-dimethyl-2,6-octadien-1-ol); phenyl ethyl alcohol (2-phenylethanol); Rhodinol™ (3,7-dimethyloct-6-en-1-ol); Sandalore™ (3-methyl-5-(2,2,3-trimethylcyclopent-3-en-1-yl)pentan-2-ol); terpineol (2-(4-methylcyclohex-3-en-1-yl)propan-2-ol); or Timberol™ (1-(2,2,6-trimethylcyclohexyl)hexan-3-ol); 2,4,7-trimethylocta-2,6-dien-1-ol, and/or [1-methyl-2(5-methylhex-4-en-2-yl)cyclopropyl]-methanol;
- aldehydes and ketones, e.g. anisaldehyde (4-methoxybenzaldehyde); alpha amyl cinnamic aldehyde (2-benzylideneheptanal); Georgywood™ (1-(1,2,8,8-tetramethyl-1,2,3,4,5,6,7,8-octahydronaphthalen-2-yl) ethanone); Hydroxycitronellal (7-hydroxy-3,7-dimethyloctanal); Iso E Super® (1-(2,3,8,8-tetramethyl-1,2,3,4,5,6,7,8-octahydronaphthalen-2-yl) ethanone); Isoraldeine® ((E)-3-methyl-4-(2,6,6-trimethylcyclohex-2-en-1-yl)but-3-en-2-one); Hedione® (methyl 3-oxo-2-pentylcyclopentaneacetate); 3-(4-isobutyl-2-methylphenyl)propanal; maltol; methyl cedryl ketone; methylionone; verbenone; and/or vanillin;
- ether and acetals, e.g. Ambrox® (3a,6,6,9a-tetramethyl-2,4,5,5a,7,8,9,9b-octahydro-1H-benzo[e][1]benzofuran); geranyl methyl ether ((2E)-1-methoxy-3,7-dimethylocta-2,6-diene); rose oxide (4-methyl-2-(2-methylprop-1-en-1-yl)tetrahydro-2H-pyran); and/or Spirambrene® (2',2',3,7,7-pentamethylspiro[bicyclo[4.1.0]heptane-2,5'-[1,3]dioxane]);

esters and lactones, e.g. benzyl acetate; cedryl acetate ((1S,6R,8aR)-1,4,4,6-tetramethyloctahydro-1H-5,8a-methanoazulen-6-yl acetate); γ-decalactone (6-pentyltetrahydro-2H-pyran-2-one); Helvetolide® (2-(1-(3,3-dimethylcyclohexyl)ethoxy)-2-methylpropyl propionate); γ-undecalactone (5-heptyloxolan-2-one); and/or vetiveryl acetate ((4,8-dimethyl-2-propan ylidene-3,3a,4,5,6,8a-hexahydro-1H-azulen-6-yl) acetate);

macrocycles, e.g. Ambrettolide ((Z)-oxacycloheptadec-10-en-2-one); ethylene brassylate (1,4-dioxacycloheptadecane-5,17-dione); and/or Exaltolide® (16-oxacyclohexadecan-1-one); and heterocycles, e.g. isobutylquinoline (2-isobutylquinoline).

The compounds and mixtures described herein may, for example, be in substantially crystalline form. By "substantially crystalline" it is meant that at least about 90 wt % of the compound or mixture is in crystalline form. For example, at least about 95 wt % or at least about 96 wt % or at least about 97 wt % or at least about 98 wt % or at least about 99 wt % of the compounds or mixtures described herein may be in crystalline form.

Alternatively, the compounds and mixtures described herein may be in solution. A diluent conventionally used in conjunction with fragrance ingredients, include ingredients such as diethyl phthalate (DEP), dipropylene glycol (DPG), isopropyl myristate (IPM), pentane-1,2-diol, triethyl citrate (TEC) and alcohol (e.g. ethanol). Optionally, the thus obtained solution may comprise an anti-oxidant adjuvant. Said anti-oxidant may be selected from Tinogard® TT (BASF), Tinogard® Q (BASF), Tinogard® TS (BASF), Tocopherol (including its isomers, CAS 59-02-9; 364-49-8; 18920-62-2; 121854-78-2), 2,6-bis(1,1-dimethylethyl)-4-methylphenol (BHT, CAS 128-37-0) and related phenols, hydroquinones (CAS 121-31-9).

There is further provided herein a fragrance composition comprising the compound of formula (I) or a mixture described herein. The compound of formula (I) or the mixture described herein comprising the compound of formula (I) and at least one (one, two, three or four) compound selected from the compounds of formula (II), (III), (IV), and (V) may, for example, be present in the consumer product in an amount ranging from about 0.001 wt % to about 10 wt % based on the total weight of the fragrance composition. For example, the compound of formula (I) or the mixture described herein may, for example, be present in the fragrance composition in an amount ranging from about 0.05 wt % to about 8 wt % or from about 0.1 wt % to about 5 wt % or from about 0.5 wt % to about 3 wt %.

There is further provided herein a consumer product comprising the compound, mixture or composition described herein. By consumer product it is meant any product that is bought to be used by an individual or household for non-business purposes.

The consumer product may, for example, be a personal care product, for example perfume extracts, eau de perfumes, eau de toilettes, aftershaves, eau de colognes, pre-shave products, splash colognes, perfumed freshening wipes, body care products, soap, liquid body wash, hair care products (e.g. shampoos, conditioners), deodorants, antiperspirants, hand creams and lotions, foot creams and lotions, hair removal creams and lotions, aftershave creams and lotions, tanning creams and lotions, and decorative cosmetic products (e.g. make-up).

The consumer product may, for example, be a cleaning product, for example, acidic, alkaline, and neutral cleaners, fabric fresheners, ironing aids, liquid detergents, fabric softeners, washing soaps, washing tablets, disinfectants (e.g. surface disinfectants), air fresheners, aerosol sprays, waxes and polishes.

The consumer product may, for example, be a homeware product, for example, candles, lamp oils, incense sticks, insecticides, repellents, and propellants.

The compound of formula (I) or the mixture comprising the compound of formula (I) and at least one (one, two, three or four) compound selected from the compounds of formula (II), (III), (IV), and (V) may, for example, be present in the consumer product in an amount ranging from about 0.0001 wt % (or even lower, e.g. 0.05 ppm or less) to about 30 wt % based on the total weight of the consumer product. In one embodiment, the compound of formula (I) or the mixture described herein may be employed in a fabric softener in an amount from 0.001 to 0.3 weight percent. In another embodiment, the compound of formula (I) or the mixture described herein may be used in fine perfumery in amounts from 0.01 to 30 weight percent (e.g. up to about 10 or up to 20 weight percent), more preferably between 0.01 and 5 weight percent. However, these values are given only by way of example, since the experienced perfumer may also achieve effects or may create novel accords with lower or higher concentrations.

There is further provided herein the use of the compound of formula (I) or the mixture comprising the compound of formula (I) and at least one compound selected from the compounds of formula (II), (III), (IV), and (V) as a fragrance ingredient. The compound of formula (I) may, for example, be used in combination with the compound of formula (II), the compound of formula (III), the compound of formula (IV), and/or the compound of formula (V). The use as a fragrance ingredient means that it is used in an amount sufficient to provide a discernible odour. The odour provided by the compound of formula (I) or the mixture comprising the compound of formula (I) and at least one compound selected from the compounds of formula (II), (III), (IV), and (V) may, for example, be a woody and/or ambery odour which may, for example, have a reduced sharp green ambery olfactory facet compared to Ambrocenide® as disclosed, e.g., in WO2015/176833.

There is further provided herein the use of the compound of formula (I) to mask or diminish one or more unpleasant olfactory facets of Ambrocenide® having the following chemical structure (WO2015/176833)

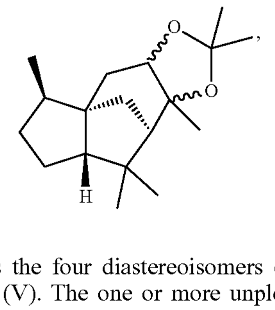

which includes the four diastereoisomers of formula (II), (III), (IV) and (V). The one or more unpleasant olfactory impressions may, for example, be a sharp green ambery olfactory facet, which can be polarizing and limit the acceptable amount that can be used in fragrance compositions.

There is further provided herein the use of the compound of formula (I) to enhance the intensity of one or more pleasant olfactory impressions of Ambrocenide®. The one or more pleasant olfactory impressions may, for example, be a woody and/or ambery odour.

The use may, for example, comprise mixing the compound of formula (I) with at least one (one, two, three, or four) compound selected from the compounds of formula (II), (III), (IV), and (V). Alternatively, the compound of formula (I) may be produced directly together with one or more of the compound of formula (II), the compound of formula (III), the compound of formula (IV), and the compound of formula (V). The compound of formula (I) may, for example, be present in an amount and/or in a ratio as described herein in relation to the mixture comprising a compound of formula (I) and one or more of the compound of formula (II), the compound of formula (III), the compound of formula (IV), and the compound of formula (V).

There is further provided herein a method of making the compound of formula (I). The method may proceed using starting materials and/or intermediate materials that include only a single stereoisomer or may proceed using starting materials and/or intermediate materials that include a mixture of stereoisomers. The end products of the method may, for example, be only a single stereoisomer or may be a mixture of stereoisomers. Different reaction conditions may be selected to produce different proportions of stereoisomers.

Particular stereoisomers of the starting materials and/or intermediate materials and/or end products may be purified by any method known to a person of ordinary skill in the art, for example, by preparative HPLC and GC, crystallization or stereoselective synthesis.

The method may, for example, comprise reacting the cedranediol of formula (Xa), or an isomeric mixture (i.e. a cedranediol of formula (X))

(Xa)

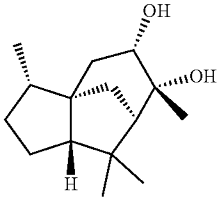

(X)

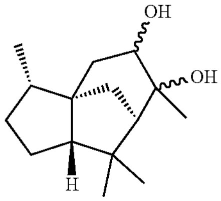

with a reactive propane derivative under suitable conditions to form the compound of formula (I). Any suitable reactive propane derivative known to those skilled in the art may be used to form the compound of formula (I).

The method may, for example, comprise reacting the cedranediol of formula (Xa) with aliphatic aldehydes and ketones using various solvents, for example toluene, cyclohexane, naphtha fractions, or diethyl ether.

The method may, for example, comprise reacting the cedranediol of formula (Xa) with dialkoxypropane, for example dimethoxypropane (e.g. 2,2-dimethoxypropane), to form the compound of formula (I). The reaction may, for example, occur under acid catalysis. The molar ratio of compounds of formula (Xa) (or the isomeric mixture) to dialkoxypropane (e.g. dimethoxypropane) may, for example, be at least about 1:5, for example from about 1:1 to about 1:4.

The compound of formula (I) may then be crystallized, for example from an aqueous alcoholic solution.

The method may, for example, comprise reacting the epi-(−)-alpha-cedrene epoxide of formula (IX), (IX)

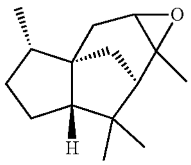

with an epoxide ring-opening agent to form the compound of formula (X).

Any suitable epoxide ring-opening agent known to persons skilled in the art may be used to form the compound of formula (X). The compound of formula (IX) may, for example, be reacted to form the compound of formula (X) by acid-catalyzed ring opening (Houben-Weyl).

The method may, for example, comprise reacting the epi-(−)-alpha-cedrene of formula (VIII), or a mixture of epi-(−)-alpha-cedrene and (−)-alpha-cedrene, (VIII)

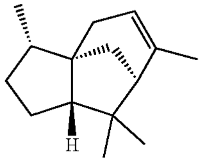

with an epoxidating agent to form the compound of formula (IX).

Any suitable epoxidating agent known to persons skilled in the art may be used to form the compound of formula (IX).

The compound of formula (VIII) may, for example, be reacted with peracetic acid to form the cedrene epoxide of formula (IX) (see, for example, Organikum, Organisch-Chemisches Grundpraktikum [Basic Practical Organic Chemistry], VEB Deutscher Verlag der Wissenschaften, Berlin, 1986, Order No. 5714576, page 568).

The epi-(−)-alpha-cedrene may, for example, be obtained using the procedure described by Niels H. Andersen et al. (Tetrahedron Lettere No. 10, 899-902, 1972). Alternatively it may be obtained from a natural source, e.g. by distillation of wood such as junipers, cypresses, sandalwood, and cedars, or distilled, pressed or chemically extracted from wood, roots an leaves from plants of, e.g. the genera *Platycladus, Yupressus, Taiwania*, and *Calocedrus.*

The composition of the mixture described herein can be influenced by careful selection of the alpha-cedrene quality as starting material. For example, the higher the amount of epi-(−)-alpha-cedrene the higher will be the amount of the compound of formula (I) in relation to the at least one compound selected from compounds of formula (II), (III), (IV), and (V). It is believed, without being bound by theory, that the stereochemical conditions remain substantially unchanged in the subsequent reaction of alpha-cedrene.

The invention is now further described with reference to the following non-limiting examples. Variations and modifications as will be readily apparent to those skilled in the art are intended to be within the scope of the present invention as defined in and by the appended claims.

EXAMPLES

Example 1—Preparation of a Composition Comprising (3aS,4aR,5S,7aS,9R,9aR)-2,2,5,8,8,9a-hexamethyloctahydro-4H-4a,9-methanoazuleno[5,6-d][1,3]dioxole of Formula (I)

A composition comprising (3aS,4aR,5S,7aS,9R,9aR)-2,2,5,8,8,9a-hexamethyloctahydro-4H-4a,9-methanoazuleno[5,6-d][1,3]dioxole of formula (I) was made via the reaction scheme shown in FIG. 1.

1.1—Preparation of a Mixture of Alpha-Cedrene Epoxides

A mixture of alpha-cedrene epoxides ((−)-alpha-cedrene epoxide and epi-(−)-alpha-cedrene epoxide) were obtained from alpha-cedrene (comprising approximately 1 wt % epi-(−)-alpha-cedrene) by epoxidation under conditions known in the art (see Organikum, Organisch-Chemisches Grundpraktikum [Basic Practical Organic Chemistry], VEB Deutscher Verlag der Wissenschaften, Berlin, 1986, Order No. 5714576, page 568).

1.2—Preparation of a Mixture of Cedrane Diols 1682.5 g of water, 317.5 g of sulfuric acid 63% and 3.0 g of Aliquat® 336 (quaternary ammonium salt known as Stark's catalyst) were added to a 2 L jacked laboratory reactor fitted with a mechanical stirrer, a cooler, and a nitrogen bubbler. This mixture was stabilized at 20° C. and the mixture of alpha cedrene epoxides prepared as above comprising (−)-α-cedrene epoxide (81.6% GC, [α] 20/D: −72.3, n 20/D: 1.4967) was fed within ten minutes. The resulting mixture was further stirred at high speed at 20° C. for 48 hours. The white precipitate was filtered and washed twice with 200 g of NaOH 2% and with 200 g of water (pH: 8). 80 g out of the obtained crude diol mixture (88.5 g) were recrystallized in 1333 mL of cyclohexane yielding 47.9 g of white crystals.

The isomeric composition of cedrane diol mixture (crystals) was 59 wt % of compound 2a (as shown in the reaction scheme in FIG. 1), 31 wt % of compound 2d (as shown in the reaction scheme in FIG. 1), and about 0.5 wt % of compound (Xa).

1.3—Preparation of a Mixture of 2,2,5,8,8,9a-hexamethyl-octahydro-4H-4a,9-methanoazuleno[5,6-d][1,3]dioxole Isomers 10.0 g of 2,2-dimethoxypropane (DMP), 12.4 g of acetone and 10.0 g of the crystallized diol mixture prepared as above were added to a 100 ml three necked round bottom flask fitted with a cooler and nitrogen bubbler. 10.0 g of a solution of technical sulfuric acid in acetone (1.08 g in 40 g) were fed within 2 hours while keeping the temperature under 30° C. The resulting mixture was further stirred at 20° C. for 3 hours, at which point another 2.0 g of the sulfuric acid solution in acetone was slowly added. After additional stirring for 2 hours at 22° C., the mixture was quenched with an aqueous sodium carbonate solution and most of the lights were evaporated under vacuum.

The residues were retaken in methyl tertiary-butyl ether (MTBE) and water and the organic layer was concentrated. The residues were then diluted with cold n-heptane and filtered. The filtrate was evaporated and recrystallized in an ethanol water mixture.

The isomeric mixture obtained was 96.4 wt % of the compound of formula (II) and 0.2 wt % of the compound of formula (I) as described herein.

Example 2—Isolation of (3aS,4aR,5S,7aS,9R,9aR)-2,2,5,8,8,9a-hexamethyloctahydro-4H-4a,9-methanoazuleno[5,6-d][1,3]dioxole (Formula (I))

(3aS,4aR,5S,7aS,9R,9aR)-2,2,5,8,8,9a-hexamethyloctahydro-4H-4a,9-methanoazuleno[5,6-d][1,3]dioxole of formula (I) was isolated by preparative gas chromatography from the recrystallized mixture obtained in Example 1.3.

The isolated fractions were then identified by NMR.

(3aS,4aR,5S,7aS,9R,9aR)-2,2,5,8,8,9a-hexamethyloctahydro-4H-4a,9-methanoazuleno[5,6-d][1,3]dioxole of formula (I) was assigned its structure on the basis of the following NMR results.

$^{1}$H NMR ($C_6D_6$, 600 MHz): 4.02 (t, J=7.7, 1H), 2.03 (dd, J=13.2, 7.3, 1H), 1.97-1.94 (m, 2H), 1.62-1.56 (m, 1H), 1.60 (s, 3H), 1.58 (s, 3H), 1.54-1.50 (m, 1H), 1.52 (s, 3H), 1.45-1.35 (m, 3H), 1.25-1.18 (m, 2H), 1.14-1.11 (m, 1H), 0.97 (s, 3H), 0.87 (d, J=6.7, 3H), 0.85 (s, 3H).

$^{13}$C NMR ($C_6D_6$, 150 MHz): 108.7, 84.9, 78.7, 57.3, 55.8, 53.9, 44.0, 43.1, 42.3, 33.5, 31.7, 30.9, 30.3, 29.8, 27.7, 27.6, 24.4, 13.7.

Example 3—Sensory Analysis

The odour profile of the compound of formula (I) obtained in Example 2 and the mixture obtained in Example 1 was evaluated by perfumers. It was surprisingly found that the soft woody ambery quality of the compound of formula (I) combines nicely with Ambrocenide®. It reinforces the original woody ambery character of Ambrocenide® and softens its sharp green ambery facet. As a result, the mixture obtained in Example 1 is more versatile and easier to dose in fragrance composition, whilst still delivering the desirable woody ambery character and performance.

Example 4: Fragrance Composition

| Compound/Ingredient | parts by weight 1/1000 |
|---|---|
| 10-UNDECENAL | 4 |
| AUBEPINE PARA CRESOL (4-methoxybenzaldehyde) | 10 |
| BENZYL ACETATE | 45 |
| BOURGEONAL (3-(4-tertbutylpheny)-propanal) | 10 |
| CINNAMIC ALCOHOL (3-phenyl-2-propen-1-ol) | 20 |
| CITRONELLOL (3,7-dimethyl-6-octen-1-ol) | 80 |
| COSMONE (E/Z 3-methyl-5-cyclotetradecen-1-one) | 5 |
| DIHYDRO EUGENOL (2-methoxy-4-propylphenol) | 3 |
| EBANOL (3-methyl-5-(2,2,3-trimethyl-3-cyclopenten-1-yl)-4-penten-2-ol) | 20 |
| ETHYL VANILLIN (3-ethoxy-4-hydroxybenzaldehyde) | 3 |
| GALAXOLIDE (1,3,4,6,7,8-hexahydro-4,6,6,7,8,8-hexamethylindeno(5,6-c)pyran) | 150 |
| GARDENOL (1-phenylethyl acetate) | 10 |
| HEDIONE (methyl 3-oxo-2-pentylcyclopentaneacetate) | 30 |
| HEXYL CINNAMIC ALDEHYDE (2-hexyl-3-phenyl-2-propenal (trans & cis)) | 80 |
| ISO E SUPER (1-(2,3,8,8-tetramethyl-1,2,3,4,5,6,7,8-octahydronaphthalen-2-yl)ethanone) | 110 |
| ISOEUGENOL (2-methoxy-4-propenylphenol) | 4 |
| ISORALDEINE 70 ((E)-3-methyl-4-(2,6,6-trimethylcyclohex-2-en-1-yl)but-3-en-2-one) | 120 |
| LILIAL (2-methyl-3-(4-(1,1-dimethylethyl)phenyl)propanal) | 60 |
| LINALOOL (3,7-dimethylocta-1,6-dien-3-ol) | 80 |

-continued

| Compound/Ingredient | parts by weight 1/1000 |
|---|---|
| METHYL OCTYNE CARBONATE (methyl 2-nonynoate) | 1 |
| 2-PHENYLETHANOL | 80 |
| 3-PHENYLPROPANOL | 3 |
| TERPINYL ACETATE (3-cyclohexene-1-methanol,alpha,alpha,4-trimethyl-,acetate) | 30 |
| TRICYCLAL (2,4-dimethyl-3-cyclohexene-1-carbaldehyde (Z)) | 1 |
| UNDECAVERTOL (4-methyl-3-decen-5-ol) | 5 |
| VIRIDINE (phenylacetaldehyde dimethyl acetal) | 1 |
| YLANG YLANG ess. | 15 |
| DIPROPYLENE GLYCOL (DPG) | 20 |
| Total: | 1000 |

The fragrance possesses a cosmetic creamy feeling, with a classical floral aldehydic structure, a musky powdery soft base note, and a modern green muguet violet opening. The fragrance is, e.g., suitable to fragrance a soap at a dosage of about 1.5 wt %.

By replacing 2 parts of DPG in the fragrance composition above with the crystalized mixture of Example 1, the overall olfactive impact is boosted and the general olfactive character results more balanced, more feminine and complex. When admixed, e.g., with a soap base, the odor performance is clearly improved as well.

The invention claimed is:

1. A fragrance ingredient comprising (3aS,4aR,5S,7aS,9R,9aR)-2,2,5,8,8,9a-hexamethyloctahydro-4H-4a,9-methanoazuleno[5,6-d][1,3]dioxole of formula (I)

(I)

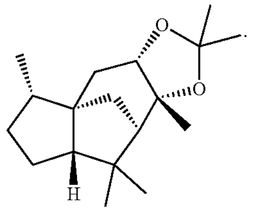

2. A fragrance composition comprising an isomeric mixture of (3aS,4aR,5S,7aS,9R,9aR)-2,2,5,8,8,9a-hexamethyloctahydro-4H-4a, 9-methanoazuleno[5,6-d][1,3]dioxole of formula (I)

(I)

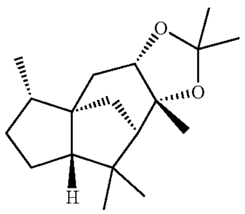

and at least one compound selected from compounds of formula (II), (III), (IV) and (V)

(II)

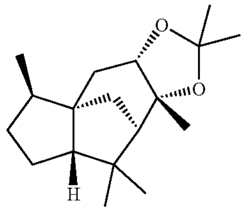

(III)

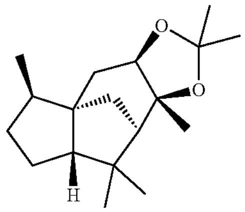

(IV)

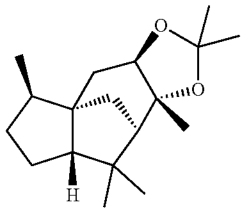

(V)

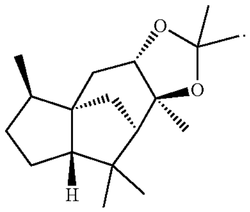 [SMILES: C[C@@H]1CC[C@H]2C(C)(C)[C@H]3C[C@@]12CC1OC(C)(C)OC13C]

3. The composition of claim 2 in substantially crystalline form.

4. The composition of claim 2, wherein the isomeric mixture comprises a compound of formula (II).

5. The composition of claim 4, wherein the weight ratio of the compound of formula (I) to the compound of formula (II) ranges from 0.01:99.99 to 5:95.

6. The composition of claim 2, wherein the isomeric mixture does not comprise a compound of formula (III).

7. A consumer product comprising the composition of claim 2.

* * * * *